United States Patent
Graham

(10) Patent No.: US 6,887,076 B2
(45) Date of Patent: May 3, 2005

(54) INTERMAXILLARY FORCE SYSTEM

(76) Inventor: Neil John Graham, 6017 Lido La., Long Beach, CA (US) 90803

(*) Notice: Subject to any disclaimer, the term of this patent is extended or adjusted under 35 U.S.C. 154(b) by 264 days.

(21) Appl. No.: 10/277,692

(22) Filed: Oct. 23, 2002

(65) Prior Publication Data
US 2004/0081937 A1 Apr. 29, 2004

(51) Int. Cl.[7] .................................................. A61C 7/36
(52) U.S. Cl. .......................................................... 433/19
(58) Field of Search .............................. 433/18, 19, 21, 433/22

(56) References Cited

U.S. PATENT DOCUMENTS 3,654,702 A * 4/1972 Kelly, Jr. ...................... 433/19
3,921,295 A * 11/1975 James ........................... 433/21
4,074,433 A * 2/1978 Nelson .......................... 433/19
5,846,074 A * 12/1998 Klapper ........................ 433/19

OTHER PUBLICATIONS

Orthoorganizers catalog this year p. 75 www.orthoorganizers.com.
Sullivan–Schein Dental Catalog 2002 p. 451 www.sullivan-schein.com.
GAC International, Inc. current cataloge page with Sentalloy Springs http://gacintl.com.

* cited by examiner

Primary Examiner—Ralph A. Lewis
(74) Attorney, Agent, or Firm—Neil John Graham

(57) ABSTRACT

A permanently mounted orthodontic intermaxillary constant force system wherein the force producing portions are attached to the orthodontic appliance in one jaw and small flexible cables transmit the forces to the patient's opposite jaw.

19 Claims, 3 Drawing Sheets

INTERMAXILLARY FORCE SYSTEM

FIELD OF THE INVENTION

The present invention is directed to a device for applying intermaxillary force from one jaw to another during orthodontic procedures where the intermaxillary connection is performed using fine cables.

BACKGROUND OF THE INVENTION

Orthodontic procedures for straightening teeth involve fixed orthodontic appliances wherein forces are often applied between the upper and lower jaws in order to correct the patient's bite. The predominant method used requires the patient's cooperation, wherein the patient repeatedly places latex rubber bands in selected positions. The latex rubber bands quickly lose their elasticity, thereby requiring the patient to repeatedly replace the latex bands. The patient's use of the bands affects treatment progress, length, and the results obtained. The uncooperative patient becomes a problem for the orthodontist.

The orthodontic profession has sought methods of applying the intermaxillary forces by seeking devices that could be permanently attached; thereby, eliminating patient cooperation. A primary requirement of a permanent force is that it maintain its elasticity. Latex loses 25% of its elasticity in the first 24 hours. The best non-latex material loses 40% of its elasticity in 24 hours. Coiled springs retain their elasticity and have been permanently placed. These springs have been open and closed coil in configuration. A close coiled spring is elongated to produce force wherein an open coiled spring is compressed to produce force. In order to produce force from one jaw to another the springs have been attached from one jaw to another, thus crossing the chewing plane of the teeth. The disadvantages of the coiled springs worn intermaxillary are that they are bulky, uncomfortable, and prone to damage during mastication. The bulkiness of the springs makes their use in the front of the mouth impossible.

SUMMARY OF THE INVENTION

In order to better understand the invention some dental terminology should be explained. An orthodontic appliance consists of a series of orthodontic brackets attached to a patient's teeth. The following dental terminology is used: buccal is towards the patient's teeth; lingual is towards the tongue; gingival is towards the gums; anterior is towards the front of the mouth; posterior is towards the back of the mouth; incisors are the front teeth; molars are the back teeth; maxilla is the upper jaw; mandible is the lower jaw; and intermaxillary is between the jaws. A bracket has a central slot which receives an archwire. The archwire is the force which actually aligns the teeth. The bracket has gingival and occlusal wings which are used to ligate the archwire to the bracket.

The present invention is directed to a permanently attached device wherein the force generating portion is attached to the orthodontic appliance within a single jaw, either the maxillary or the mandibular jaw. The intermaxillary force device comprises a longitudinal hollow tube with an inner and outer diameter and opposing ends, a first end and a second end. In the preferred embodiment, the longitudinal tube contains within its interior a longitudinal open coiled spring within its first and second ends extending almost the length of the longitudinal tube. The tube contains two v-grooved roller bearings, one at each end of the spring. A v-grooved pulley is mounted to the first end of the tube on a shaft mounted to the tube at a right angle to the tube's axis. Adjacent to the first end bearing the tube is constricted to form a seat for the first end of the internal coiled spring At the second end of the spring a second v-grooved pulley is housed and mounted to a shaft within a ball which is seated within the second end of the internal spring.

A flexible cable is attached to the first of the spring and extends internally within the spring to the second end of the spring and encircles the v-groove of the second end pulley and returns internally within the spring to the v-groove at the first end of the spring. This is an important path for the string as the string travels twice the distance of compression of the spring. This allows for the opening and closing of the jaw. The jaw in the anterior opens as wide as 35 mm and moves sagitally 12 mm. The average open-coiled spring is 27 mm and will compress ⅔ of its length to 9 mm. The 18 mm of movement is not enough to allow for the 35 mm of jaw movement. The use of the second end pulley allows the cable to move twice the distance or 36 mm which is adequate for the jaw to open wide The first end of the tube has an opening in the wall allowing the cable to circle the v-grooved pulley and exit the tube to the opposing arch of teeth. In a preferred embodiment, the first end v-grooved pulley is pivotally mounted allowing the pulley to swivel to accommodate the different cable directions due to different points of cable attachment in the opposite jaw end movement of the lower jaw.

The longitudinal tube is attached to the orthodontic appliance using, in a preferred embodiment, a locking clasp which allows easy placement and removal of the longitudinal tube. The locking clasp is attached to the orthodontic appliance using a configured wire. The clasps may also be attached to a separate heavier arch wire which is in turn ligated to the orthodontic appliance.

The flexible cable may be attached to the opposing arch by tying to to a bracket, button, arch wire, or an attachable hook.

The attachable hook, in its preferred embodiment, is 3–4 mm in length and is attached to a configured 0.016 inch stainless steel wire adapted to an orthodontic bracket archwire combination.

In an alternative embodiment of the present invention, the cable returns to the arch it originated from, producing a maxillary mandibular vertical pull, as in a force in the front of the patient's mouth to close an anterior open bite.

In an alternative embodiment of the present invention, the cable is attached directly to the second end of the spring, eliminating the bearing at the second end of the spring.

In a further alternative embodiment of the invention, the spring is a close coiled spring attached to the second end of the tube.

In a further alternative embodiment of the invention, the force system, such as the coil springs, can be used without the horizontal tube.

DETAILED DESCRIPTION OF THE INVENTION

Figure 1:
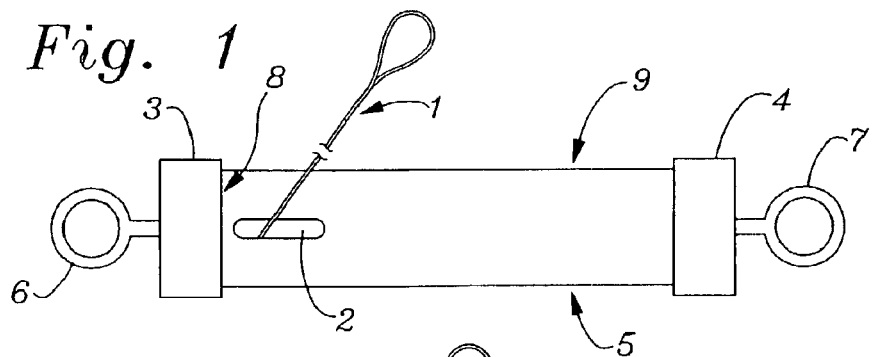
FIG. 1 is a prospective view of the intermaxillary force system.
Figure 2:
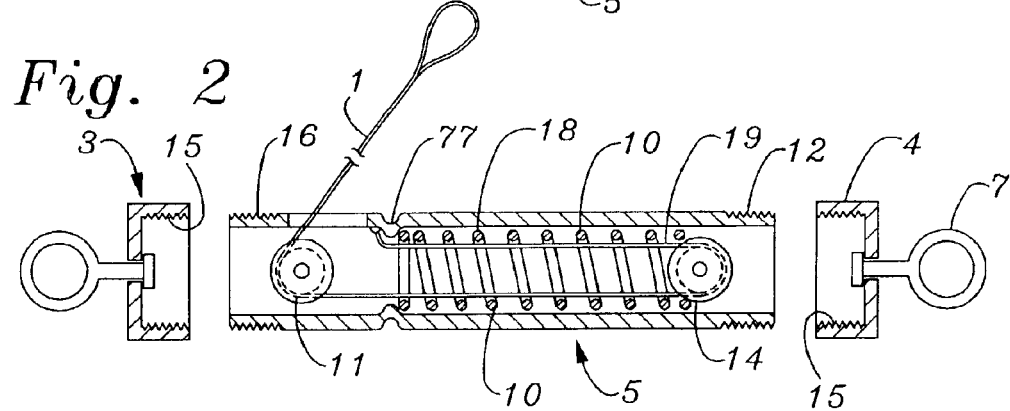
FIG. 2 is an internal view of the intermaxillary force system of FIG. 1.
Figure 3:
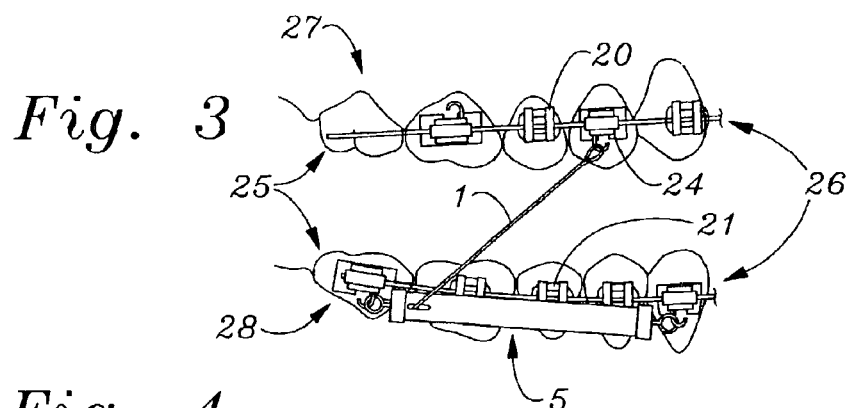
FIG. 3 is a view of the intermaxillary force system mounted to an orthodontic appliance.
Figure 6:
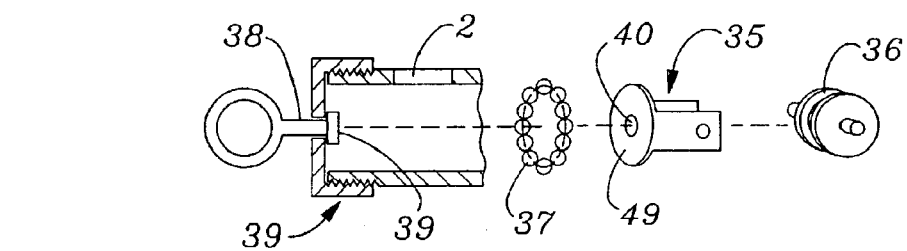
FIG. 6 is an internal view of the pivotally mounted first end v-shaped pulley.
Figure 9:
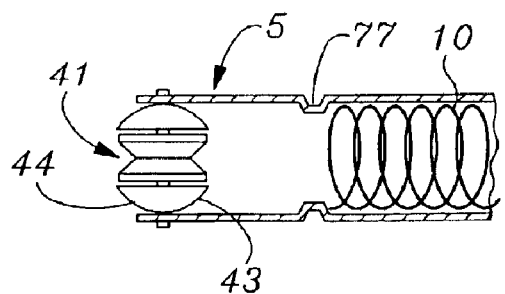
FIG. 9 is an interior view of the mounted first end v-shaped pulley.
Figure 10:
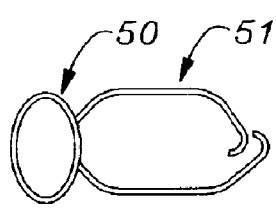
FIG. 10 is the circular clasp mounted to a wire configuration.
Figure 11:
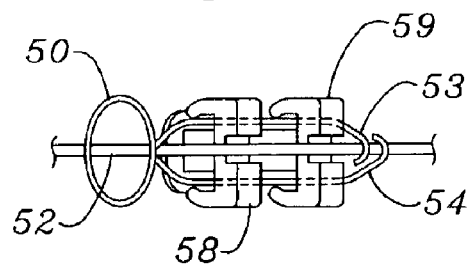
FIG. 11 the configured wire of FIG. 10 mounted on an orthodontic bracket archwire combination.

Referring to FIGS. 1–3 the intermaxillary force appliance has a longitudinal hollow tubular body 5 having sufficient length to extend from the patient's posterior molar area 25 to the anterior cuspid area 26. The tube is preferably metal. The diameter of the horizontal tube 5 may be 2–6 mm, preferably 4 mm to be comfortably worn by the patient. The horizontal tube 5 has a first 8 and second 9 end. An open coiled longitudinal spring 10 is enclosed in the horizontal tube 5 extending from the first tube end 8 to the second tube end 9. The spring 10 has a first 18 and second 19 end to correspond to the first 8 and second end 10 of the tube 5. The external diameter of the spring is less than the internal diameter of the tube 5, allowing the spring 10 to be compressed. A sphere 14 the same diameter as the spring 10 rests at the second spring end 19. The horizontal tube 5 is externally threaded at the first 16 and second 15 ends. An internally threaded cap, the first end cap 12, is threaded onto the first horizontal tube end external thread 16. A second end cap 4 is threaded over the second horizontal tube threaded end 15. The first and second end caps have eyelets 6–7 for ligation. Referring to FIG. 6, in a preferred embodiment, the first end cap 3 has an interior wherein a 4 mm shaft 38, 1–2 mm in diameter, is mounted centrally in the long axis of the horizontal tube 5. Pivotally mounted upon the shaft is a v-shaped roller bearing 36 mounted to mounting brackets 35 attached to a pedestal base 49. The pedestal base 49 has a central hole 40 which receives the shaft 38. The shaft 38 has an end 39 which extends into the horizontal tube 5 wherein the end 39 is enlarged locking the pedestal base 49 to the first end cap 3. Spherical bearings 37 may be placed between the pedestal base 49 and the first end cap 3, enhancing the rotation of the v-shaped roller bearing 36. Adjacent to the pivotally mounted first end roller bearing 11 is an opening 2 in the wall of the horizontal tube 5. The first end spherical bearing 36 is mounted offset 35 towards this opening 2. In FIG. 9, adjacent to the tube opening 12, the horizontal tube 5 is circumferentially narrowed 77 to form a seat for the first end 18 of the spring 10.

Figure 4:
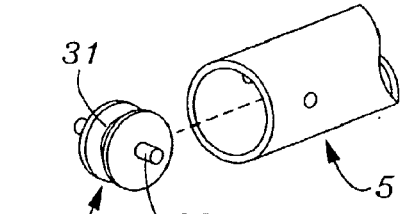
FIG. 4 is an end view of the of the mounted first end v-shaped pulley.
Figure 5:
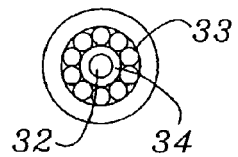
FIG. 5 is a side view of the v-shaped pulley.

Referring to FIG. 4, another embodiment of the first end pulley 30 is mounted to a central shaft 32 mounted to the walls of the horizontal tube 5. The v-shaped pulley is shown in FIGS. 30–31 4, 5, and 8. A central shaft housing 34 is surrounded by roller bearings 33. The pulley is v-shaped to receive a cable.

Referring to FIGS. 1–3 a flexible cable 1 0.015–0.030 inch in diameter is attached at the first tube end 8 and extends through the center of the spring to the second end of the spring 19, wraps around the v-grooved pulley 14 at the second end and returns to through the center of the spring to the first horizontal tube end 8, wraps around to his first end v-shaped pulley 11, and exits the horizontal tube through the opening 2 in the wall of the horizontal tube 5.

A preferred embodiment of the cable is a 0.016 inch diameter 60 pound test microfilament line called POWER PRO® sold by Innovative Textiles, inc. The cable is made from SPECTRA® FIBER from Honeywell International.

Figure 12:
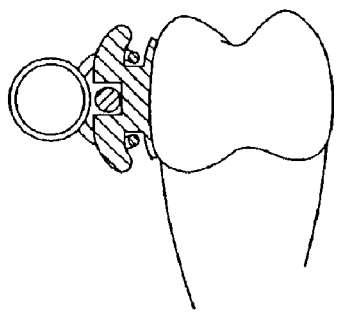
FIG. 12 is a cross-sectional view FIG. 11.
Figure 13:
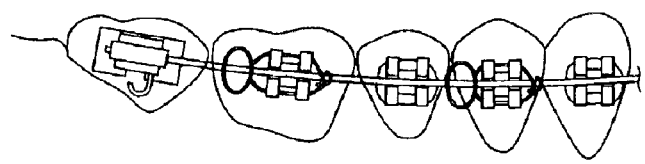
FIG. 13 is a view of the clasp wire configuration mounted in the mouth.

The horizontal tube 5 assembly is mounted, as shown in FIGS. 3 and 12, positioned between the orthodontic brackets and the patient's cheek. The horizontal tube 5 is positioned slightly gingival FIG. 12 to the central position of the bracket 56 to keep the tube out of occlusal contact with the patient's opposing teeth. Referring to FIG. 3, the cable I is shown exiting the first end of the tube 8 and attaching to the patient's upper arch in the cuspid area 24. The length of the cable is adjusted to compress the spring sufficiently to apply pressure from the patient's lower dental arch to the anterior of the patient's upper arch. This force would move patient's upper teeth inward, correcting the bite.

Figure 7:
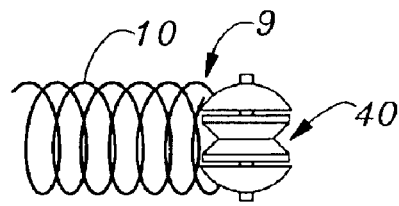
FIG. 7 is a view of the spherically mounted second end v-shaped pulley resting on the second end of the coiled spring.
Figure 8:
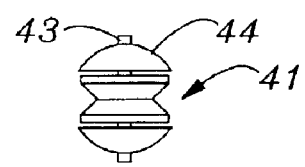
FIG. 8 is another view of the pulley of FIG. 7.

Referring to FIGS. 2 and 7, in a preferred embodiment, there is a v-shaped roller bearing 41 embedded within a sphere 14 mounted on the second end 19 of the coiled spring 10. The sphere 14 and v-shaped pulley 41 are mounted on an axial mounting shaft 43. The cable 1 originates at first end of the horizontal tube 8 and travels through the interior of the coiled spring, engages the second end pulley 14 and returns to the first end pulley 11. This pulley arrangement allows the cable to have twice the movement of the compression distance of the spring, allowing for full motion of the lower jaw.

The advantage of this appliance is that it is permanently attached eliminating the variable of patient cooperation. The continuous force reduces the time the patient will spend in orthodontic appliances, reduces the orthodontist's chair time, and increases the success rate of the orthodontic treatment.

Referring to FIGS. 10–13 a configured wire 50–54 attaches the horizontal tube 5 to the orthodontic bracket 56 archwire 52 combination. An orthodontic bracket has a central horizontal slot for the archwire and occlusal 59 and gingival 58 wings for ligating the archwire 52. The configured wire has a clasp portion 50 and a portion 51 which engages the archwire and bracket.

The horizontal tube assembly 5 is mounted to the orthodontic appliance, in a preferred embodiment, using clasps 50 and 53 which grip the horizontal tube 5 combination. The clamps are secured to the bracket archwire combination. The mounting of the clasp 50 and 53 to the bracket is done by using a 0.016 inch wire which is attached to the clasp and is configured to engage the occlusal tie wings 59 of the orthodontic bracket, pass over the buccal surface of the archwire, and return under the gingival tie wings 58 of the orthodontic bracket 56 to be attached to the clasp 50 and 53. The wire has a break in it where it passes over the archwire, resulting in two ends. Each wire is configured as a small C-hook 53 which rests over and engages the buccal of the archwire.

Figure 14:
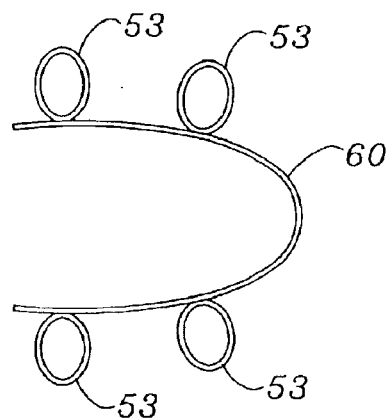
FIG. 14 is a view of the clasps mounted to a heavy archwire.
Figure 15:
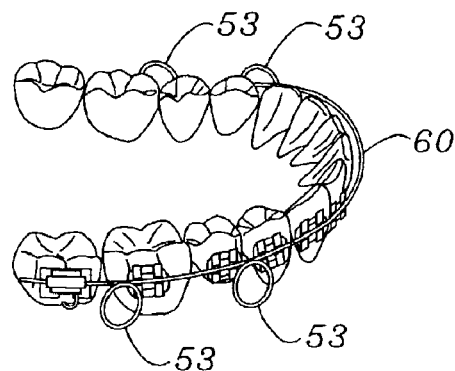
FIG. 15 is a view of the apparatus of FIG. 14 mounted in the mouth.
Figure 16A:
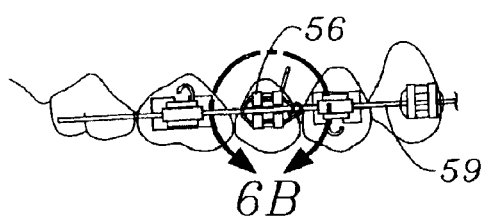
FIG. 16 is a view of the configured wire with a hook as it is placed in the mouth.
Figure 16B:
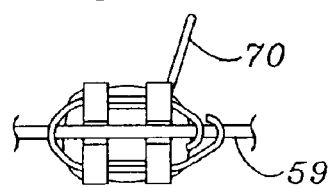

Referring to FIGS. 14–15 another embodiment in mounting the horizontal tube assembly 5 to the orthodontic appliance is to mount the horizontal tube 5 by soldering or attaching the tube to an overlay archwire 60. The overlay archwire 60 is bent to the same arch form as the archwire 52 using the same tie-wires used for the existing archwire 52

Figure 18:
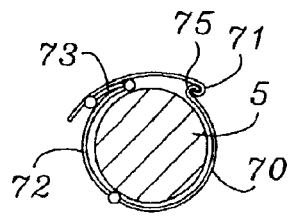
FIG. 18 is a view of the locking clamp in an open position.
Figure 19:
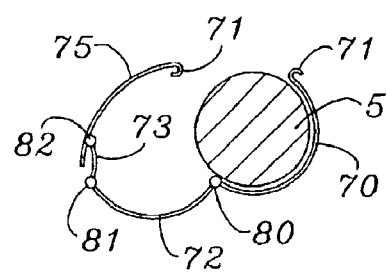
FIG. 19 is a view of the locking clamp of FIG. 18 in a closed position.

A preferred embodiment of the horizontal tube clasp is in FIGS. 18–19 wherein the clasp is a locking clasp comprising a c-clasp 70 with a lip at one end 71. The other end of the c-clasp 70 is hinged 80 to a first smaller curved section 72 which is in turn hinged at its free end 81 to a smaller second curved section 73 to which is hinged at its free end 82 to the center of a third c-section 74 which has a lip at its free end 75 adjacent the c-hook lip 71. FIG. 18 shows the clasp open allowing easy insertion or removal of the horizontal tube. FIG. 19 shows the clasp closed to a locked position.

Figure 17:
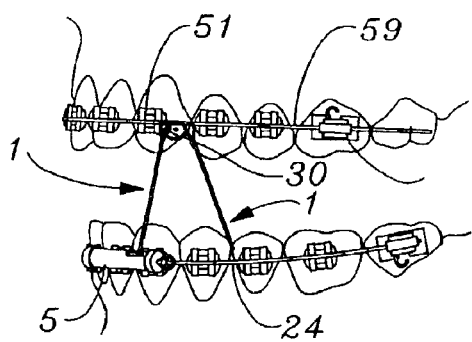
FIG. 17 is a view of the horizontal tube mounted with the first end in the front of the mouth.

Referring to another configuration of the intermaxillary force appliance in FIG. 17 the horizontal tube 5 ends are reversed wherein the cable 1 exits the horizontal tube 5 at the front of mouth. The cable would be used in this configuration for class III, or underbite correction. This embodiment can also be used by attaching the cable straight upwards to the anterior of the patient's mouth FIG. 17, for use in closing an anterior open bite.

What is claimed:

1. An intermaxillary force system for applying permanent intermaxillary forces during orthodontic treatment comprising:
    a hollow longitudinal tube having a first and second end, a wall with an outer and inner circumference wherein the tube is attached to an orthodontic appliance to be positioned within a single jaw;
    a force producing means within the tube for producing tooth movement;
    a flexible cable connected to the internal force producing means wherein the cable exits the tube at the first end and is attached to the orthodontic appliance to be positioned in the opposite jaw for producing tooth movement pressure between the jaws;
    an attaching means for securing the horizontal tube to the orthodontic appliance.

2. The intermaxillary force system according to claim 1 wherein the force producing means is a longitudinal open coiled spring with a first and second end, an interior and an outer diameter, the outer diameter being slightly smaller than the inner circumference of the longitudinal tube wherein the spring is placed in the tube and the cable is attached to the spring which is compressed producing a pulling force upon the cable.

3. The intermaxillary force system according to claim 2 wherein a sphere with the same diameter as the outer diameter of the coiled spring containing an axially mounted grooved pulley is mounted on the second end of the spring whereby the cable is mounted to the first end of the spring, corresponding to the first end of the tube, and the cable travels through the spring interior to the second end of the spring, around the grooved pulley and returns to the first end of the tube where it exits the tube to the opposite arch.

4. The intermaxillary force system according to claim 1 wherein the outer circumference of the longitudinal tube is threaded at the first and second ends.

5. The intermaxillary force system according to claim 4 wherein internally threaded caps are threaded over the externally threaded first and second tube ends, each cap has an externally centrally mounted eyelet 2 millimeter in diameter, the cap at the first tube end has a central shaft extending 2–4 millimeters into the longitudinal tube.

6. The intermaxillary force system according to claim 3 wherein there is a lateral opening in the wall of the first end of the tube.

7. The intermaxillary force system according to claim 6 wherein a grooved pulley, the same size and shape as the second end pulley, mounted on a pedestal base slightly offset to the axial center of the base and adjacent to the lateral opening, the pedestal base is pivotally mounted to the central shaft of the first end cap with ball bearings between the pedestal and the cap, whereby the cable returns from the first end, travels around the first end pulley and exits through the lateral opening, the pivoting of the enabling various directional attachments of the cable to the opposite jaw and allowing for movements of the lower jaw.

8. The intermaxillary force system according to claim 2 wherein the open coiled spring is sufficiently open to allow compression to at least one-third of the coiled spring's length.

9. An intermaxillary force system for applying permanent intermaxillary force during orthodontic treatment comprising:
    a longitudinal thin walled tube with first and second ends, a length sufficient to extend from a patient's molars to the incisors, an opening in the wall of the tube near the first end;
    a coiled longitudinal spring within the tube;
    a grooved pulley at the first end of the tube adjacent to the lateral opening; and
    a cable attached to the spring wherein the cable enters the pulley groove and exits the tube through the adjacent lateral opening and is attached at a point on the orthodontic appliance of the opposite dental arch.

10. The intermaxillary force system according to claim 9 wherein the cable is a 0.020 inch gauge woven with the test strength of 60 pounds.

11. The intermaxillary force system as in claim 9 wherein the longitudinal tube is comprised of metal.

12. The intermaxillary force system as in claim 9 wherein the horizontal tube is comprised of stainless steel.

13. The intermaxillary force system of claim 9 wherein the attachment of the cable in the opposite arch is an attachable hook comprising:
    a 0.016 inch diameter stainless steel wire configured to attach to the orthodontic bracket combination of the orthodontic appliance;
    a hook attached to the stainless steel wire for the attachment of the cable from the opposite arch; and
    a locking configuration of the configured arch is achieved by the wire following the following configuration:
    a hook shape to grip the buccal surface of the arch wire where the end of the hook points at the teeth;
    the wire extends gingivally towards the base of the adjacent orthodontic bracket;
    the wire turns parallel to the arch wire and engages the underside of the tie wing of the bracket;
    the wire turns towards the archwire at the opposite end of the bracket and passes over the buccal surface of the archwire;
    the wire passes towards the tooth and turns parallel to the arch wire and engages the underside of the wing of the bracket; and the wire returns to its original origin where it has a hook which engages over the buccal of the archwire and the end of the hook points back towards the teeth, wherein when the hook is engaged the wire configuration is held in a firm position in relation to orthodontic appliance.

14. The intermaxillary force system as in claim 9 wherein the longitudinal coiled spring is closed and the spring is attached to the second end of the tube, the spring length is shorter than the tube and the cable is attached to the spring end opposite the attached end wherein stretching of the spring produces force to the cable.

15. The intermaxillary force system as in claim 9 wherein the longitudinal thin walled tube is to be secured in the mouth with a circular mounted bracket which engages the tube and is then attached to an attachable stainless-steel configured wire which is in turn attached to the orthodontic appliance, the horizontal tube is to be mounted horizontally in a single jaw centered to the gingival bracket wing of the orthodontic bracket.

16. An intermaxillary force system comprising:
   a hollow longitudinal tube containing a system capable of producing a pulling force;
   a cable system attached to the pulling force system for translating the force to a point in the opposite jaw; and
   a mounted C shaped clasp system attached to the hollow longitudinal tube wherein the C shaped clasp is attached to an orthodontic appliance thereby attaching the hollow longitudinal tube to an orthodontic appliance.

17. The intermaxillary force system as in claim 16 wherein the mounted clasp for engaging the tube may be opened allowing insertion of the horizontal tube.

18. The intermaxillary force system as in claim 16 wherein the mounted C shaped clasp comprises:
   a solid C portion with first and second ends configured to fit circumferentially around the longitudinal tube less than half the diameter of the tube, allowing insertion of the tube;
   a configured first end of the C portion which is configured outwards from the circumference and turns back towards C portion to form a lip;
   a first smaller curved section with two ends is curved to fit the longitudinal tube is hinged to;
   a second smaller curved section with two ends is hinged to the free end of the first section, the second curved section is in turn hinged at its free end; and
   a third smaller curved section with a center and two ends wherein the center is hinged to the free end hinge of the second smaller section, wherein the third section free end is curved towards the tube, the hooked end engages the curved hook of the first C portion, the third section is held at an angle to the tube, the third portion is then pressed towards the tube in the direction of the second C portion thus firmly engaging the tube and locking the tube into position.

19. The intermaxillary force system as in claim 16 wherein the mounted C shaped clasps are attached to a wire shaped the same as the orthodontic arch wire, but heavier gauge, 0.025 inch to 0.055 inch diameter, wherein the wire is connected to the orthodontic appliance by tying to the arch wire or attaching it to the bracket using the same ties that ligate the archwire to the brackets.

* * * * *